United States Patent
Otsuka

(10) Patent No.: US 11,474,219 B2
(45) Date of Patent: Oct. 18, 2022

(54) ULTRASONIC PROBE, AND ULTRASONIC IMAGE DISPLAY APPARATUS

(71) Applicant: General Electric Company, Schenectady, NY (US)

(72) Inventor: Masaaki Otsuka, Hino (JP)

(73) Assignee: General Electric Company, Schenectady, NY (US)

( * ) Notice: Subject to any disclaimer, the term of this patent is extended or adjusted under 35 U.S.C. 154(b) by 945 days.

(21) Appl. No.: 16/193,879

(22) Filed: Nov. 16, 2018

(65) Prior Publication Data

US 2019/0162832 A1 May 30, 2019

(30) Foreign Application Priority Data

Nov. 30, 2017 (JP) .............................. JP2017-229844

(51) Int. Cl.
  *G01S 7/00* (2006.01)
  *G01S 7/52* (2006.01)
  *F28D 15/02* (2006.01)
  *A61B 8/00* (2006.01)

(52) U.S. Cl.
  CPC .......... *G01S 7/52079* (2013.01); *A61B 8/546* (2013.01); *F28D 15/0275* (2013.01)

(58) Field of Classification Search
  CPC ... G01S 7/52079; A61B 8/546; A61B 8/4444; A61B 8/4488; A61B 8/4455; A61B 8/00; F28D 15/0275; G10K 11/004; B06B 1/0685; B06B 1/067; B06B 2201/76; H01L 41/04; G01N 29/2437; G01N 29/32; G01N 29/223; G01N 2291/02475

USPC .......................................................... 367/188
See application file for complete search history.

(56) References Cited

U.S. PATENT DOCUMENTS

| 7,834,520 | B2 * | 11/2010 | Hu .......................... A61B 8/00 600/459 |
| 9,072,487 | B2 * | 7/2015 | Hebrard ............... G01S 7/52079 |
| 2006/0100513 | A1 * | 5/2006 | Hashimoto ............... A61B 8/00 600/437 |
| 2008/0139945 | A1 * | 6/2008 | Hu ...................... G01S 7/52017 600/459 |
| 2011/0077557 | A1 * | 3/2011 | Wing .................. B01D 19/0042 601/2 |

(Continued)

FOREIGN PATENT DOCUMENTS

| JP | 2009-297352 A | 12/2009 |
| JP | 2011-229976 A | 11/2011 |

(Continued)

OTHER PUBLICATIONS

Notification of Reasons for Refusal issued in connection with corresponding JP Application No. 2017-229844 on Oct. 23, 2018 (English Translation not available).

*Primary Examiner* — James R Hulka

(57) ABSTRACT

An ultrasonic probe including ultrasonic vibrators for transmitting ultrasound and a housing for encasing the ultrasonic vibrators. The ultrasonic probe includes a heat dissipation member encased in the housing in thermal connection with the ultrasonic vibrators and housing, and constructed separately from the housing, wherein the heat dissipation member has opposing surfaces and facing inner surfaces of the housing, the opposing surfaces being secured in close contact with the inner surfaces.

18 Claims, 4 Drawing Sheets

(56) References Cited

U.S. PATENT DOCUMENTS

2013/0301395 A1* 11/2013 Hebrard ................. A61B 8/546
　　　　　　　　　　　　　　　　　　　　　　　367/189
2015/0289852 A1* 10/2015 Cho ....................... A61B 8/546
　　　　　　　　　　　　　　　　　　　　　　　600/459
2017/0172542 A1*  6/2017 Lee ......................... A61B 8/56

FOREIGN PATENT DOCUMENTS

| JP | 2013-052023 A | 3/2013 |
| JP | 2014-516686 A | 7/2014 |
| JP | 2014-217529 A | 11/2014 |
| JP | 2015-202401 A | 11/2015 |
| JP | 2016-019556 A | 2/2016 |
| JP | 2017-093877 A | 6/2017 |
| JP | 2017-093878 A | 6/2017 |
| JP | 2017-517330 A | 6/2017 |

* cited by examiner

ULTRASONIC PROBE, AND ULTRASONIC IMAGE DISPLAY APPARATUS

FIELD OF THE INVENTION

The present invention relates to an ultrasonic probe having a heat dissipation member thermally connected with ultrasonic vibrators, and an ultrasonic image display apparatus.

BACKGROUND OF THE INVENTION

An ultrasonic probe comprises ultrasonic vibrators, an acoustic lens, and a backing layer. More particularly, the acoustic lens is disposed to abut against a subject to be examined on the side of the subject with respect to the aforesaid ultrasonic vibrators, while the aforesaid backing layer is disposed on a side opposite to the subject. The aforesaid ultrasonic vibrators are comprised of piezoelectric elements such as PZT (lead zirconate titanate), to which voltage is applied to transmit ultrasound.

In transmitting/receiving ultrasound, heat is generated in the ultrasonic vibrators. Patent Document 1 discloses an ultrasonic probe in which a thermally conductive heat spreader is disposed in a housing to prevent the heat from being transferred to the acoustic lens and raising the temperature of the lens surface.

BRIEF DESCRIPTION OF THE INVENTION

There is found in Patent Document 1 in Paragraph 0008 a description that reads "the housing 22 is molded around the metal heatspreader. In this implementation the handle portion 22 and the nosepiece 24 are molded as a single housing 22' which is formed around the heatspreader 20'." This means that the housing and metal heat spreader are monolithically molded by insert molding; however, it is necessary in insert molding to form a hole or a notch in the heat spreader for avoiding an undercut etc. The heat spreader formed with such a hole or a notch has a heat dissipating area reduced by the hole or notch.

On the other hand, a separate heat spreader and housing can avoid the aforementioned problem, although closeness of contact against each other is poor, resulting in reduced mechanical strength, or reduced heat transfer efficiency even when a thermal gasket is interventionally provided between the heat spreader and housing as described in Patent Document 1.

The invention made for solving the aforementioned problem is an ultrasonic probe comprising: ultrasonic vibrators for transmitting ultrasound; a housing for encasing therein said ultrasonic vibrators; and a heat dissipation member constructed separately from said housing, and encased in said housing in thermal connection with said ultrasonic vibrators and said housing, wherein said heat dissipation member has an opposing surface facing an inner surface of said housing, said opposing surface being secured in close contact with said inner surface.

According to the invention in the aspect described above, the housing and the heat dissipation member are separately constructed, unlike one monolithically molded by insert molding, and therefore, there is no need for a hole or a notch provided in the heat dissipation member, so that the heat dissipation area can be saved. Moreover, since the inner surface of the housing and the opposing surface of the heat dissipation member are secured in close contact with each other, mechanical strength can be improved, and heat can be efficiently transferred from the heat dissipation member to the housing.

DETAILED DESCRIPTION OF THE INVENTION

Figure 1:
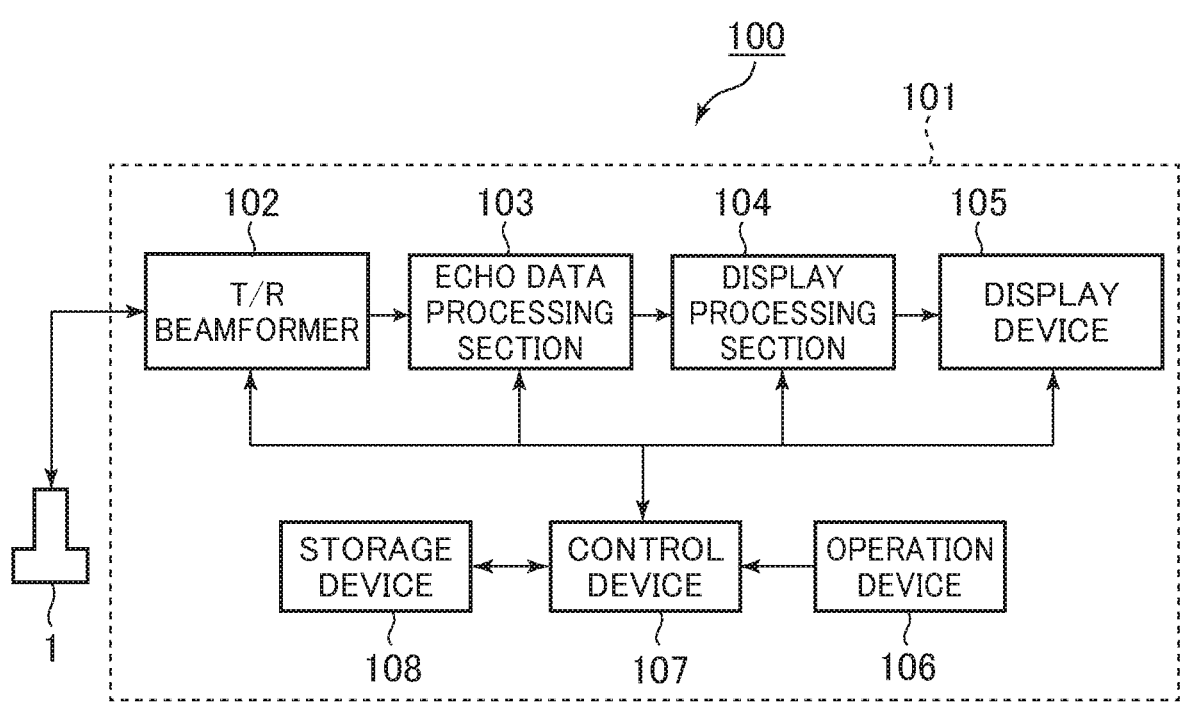
FIG. 1 A block diagram showing an exemplary embodiment of an ultrasonic diagnostic apparatus in accordance with the present invention.

Now several embodiments of the present invention will be described hereinbelow. An ultrasonic diagnostic apparatus 100 shown in FIG. 1 is an example of the ultrasonic image display apparatus in the present invention, and it has an ultrasonic probe 1, and an apparatus main unit 101 to which the ultrasonic probe 1 is connected.

The aforesaid apparatus main unit 101 comprises a transmission/reception (T/R) beamformer 102, an echo data processing section 103, a display processing section 104, a display device 105, an operating device 106, a control device 107, and a storage device 108.

The T/R beamformer 102 supplies to the ultrasonic probe 1 electric signals for transmitting ultrasound from the ultrasonic probe 1 under specific scan conditions based on control signals from the control section 107. The T/R beamformer 102 also applies signal processing, including A/D conversion, phased addition, etc., to echo signals received at the ultrasonic probe 1.

The echo data processing section 103 applies processing for producing an ultrasonic image to echo data output from the T/R beamformer 102. For example, the echo data processing section 103 performs B-mode processing, such as logarithmic compression processing and envelope detection processing, to create B-mode data.

The display processing section 104 scan-converts the data input from the echo data processing section 103 by a scan converter to create ultrasonic image data, based on which it displays an ultrasonic image on the display device 105. The display processing section 104 creates, for example, B-mode image data based on the B-mode data, and displays a B-mode image on the display device 105.

The display device 105 is constructed from an LCD (Liquid Crystal Display) or a CRT (Cathode Ray Tube), for example. The operating device 106 is constructed including switches, a keyboard, a pointing device, etc. (omitted in the drawing), for an operator to input a command and/or information.

The control device 107 is a processor, such as a CPU (Central Processing Unit). The control device 8 loads programs stored in the storage device 9 to control several sections in the ultrasonic diagnostic apparatus 100.

The storage device 108 includes non-transitory storage media and transitory storage media. The non-transitory storage media are, for example, non-volatile storage media, such as a HDD (Hard Disk Drive) and ROM (Read Only Memory). The non-transitory storage media may include a portable storage medium, such as a CD (Compact Disk) and a DVD (Digital Versatile Disk).

The transitory storage media are volatile storage media, such as RAM (Random Access Memory).

Figure 2:
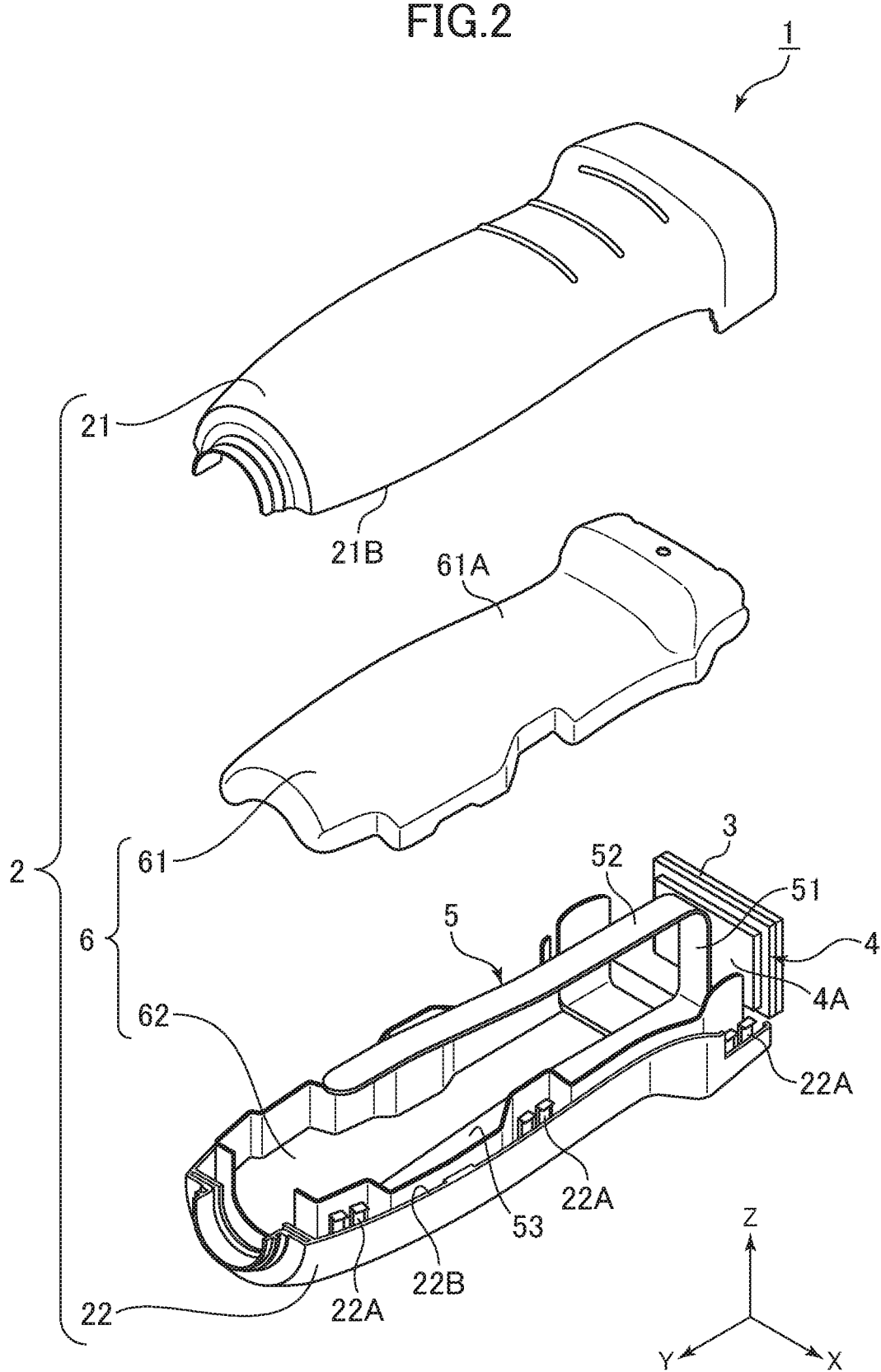
FIG. 2 An exploded perspective view of an ultrasonic probe.
Figure 3:
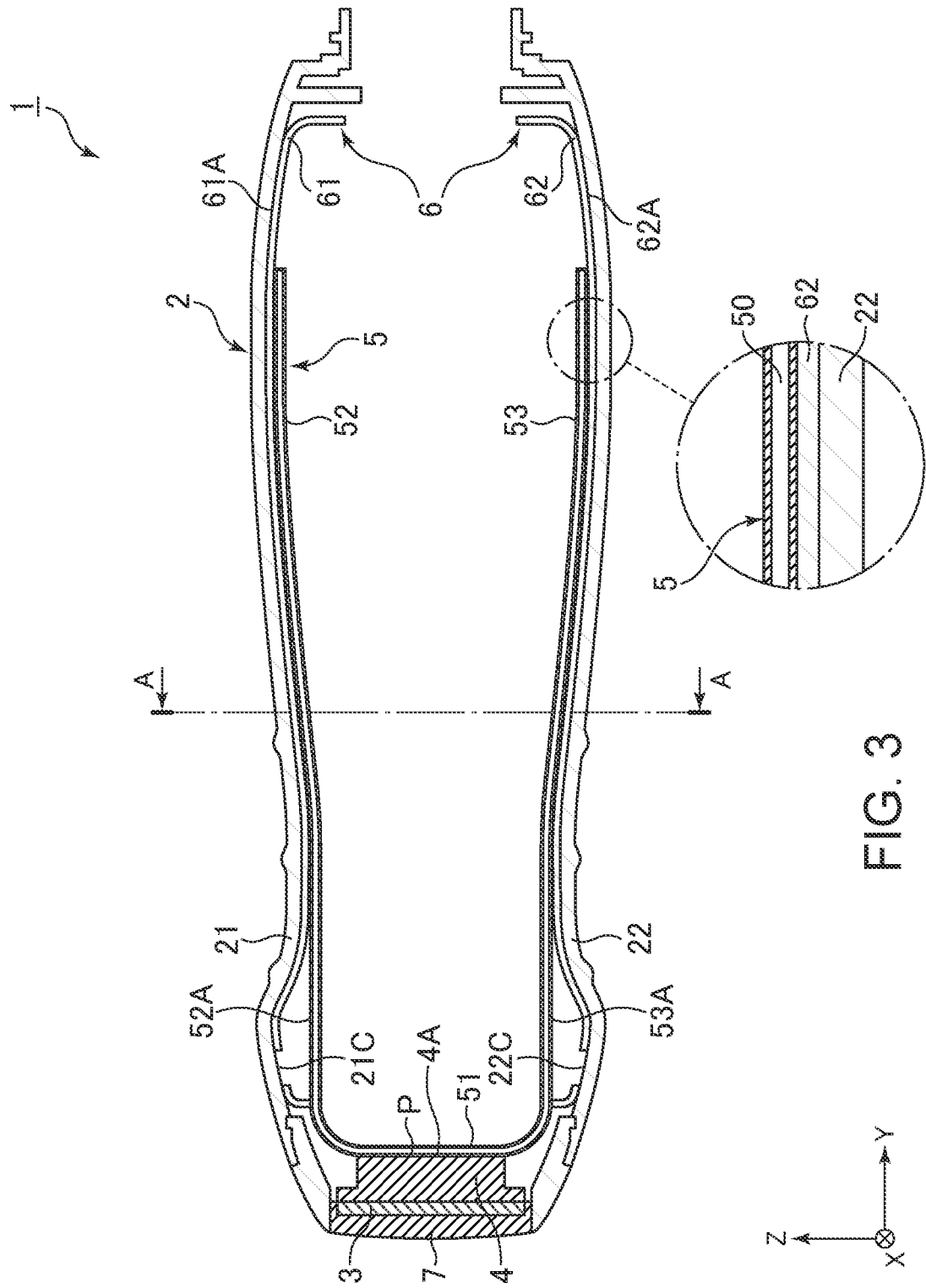
FIG. 3 A vertical cross-sectional view of the ultrasonic probe.
Figure 4:
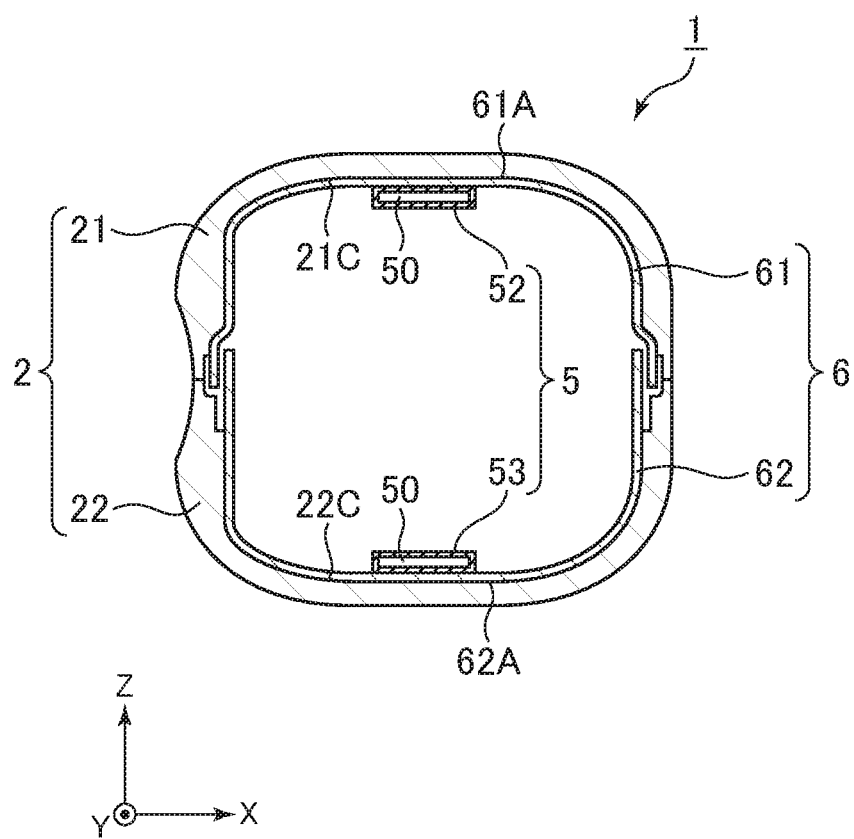
FIG. 4 An A-A cross-sectional view of FIG. 3.

The ultrasonic probe 1 will now be described with reference to FIGS. 2 to 4. FIGS. 2 to 4 show only a main portion of the ultrasonic probe 1. Cross-sectional views in FIGS. 3 and 4 show only a cut end surface.

The ultrasonic probe 1 performs a scan with ultrasound on a subject to be examined. The ultrasonic probe 1 also receives echo signals of ultrasound. The ultrasonic probe 1 comprises a housing 2, ultrasonic vibrators 3 encased in the housing 2, a backing layer 4, a thermal-conducting member 5, a heat dissipation member 6, and an acoustic lens 7 (shown only in FIG. 3). The ultrasonic probe 1 performs transmission/reception of ultrasound with the acoustic lens 7 abutted against a body surface of the subject. It should be noted that only main components are shown in FIGS. 2 to 4, and the ultrasonic probe 1 may comprise other components.

The housing 2 is comprised of a pair of a first housing member 21 and a second housing member 22. The first housing member 21 and second housing member 22 are each formed generally in a C shape in a cross section orthogonal to a longitudinal direction of the housing 2, as shown in FIG. 4.

The second housing member 22 is provided with locking members 22A, and the first housing member 21 is provided with locked members with which the locking members 22A are engaged, although not specifically shown. The first housing member 21 and second housing member 22 are joined together at respective opposing joint interfaces 21B, 22B with the locking members 22A engaged with the locked members. The housing 2 is an exemplary embodiment of the housing in the present invention. The first housing member 21 is an exemplary embodiment of the first housing member in the present invention, and the second housing member 22 is an exemplary embodiment of the second housing member in the present invention. The joint interfaces 21B, 22B are an exemplary embodiment of the joint interfaces in the present invention.

The ultrasonic vibrators 3 have piezoelectric elements of PZT or the like, and transmit ultrasound. While the detailed configuration of the ultrasonic vibrators 3 is omitted in the drawing, the plurality of ultrasonic vibrators 3 are arranged in an X-axis direction. The ultrasonic vibrators 3 are an exemplary embodiment of the ultrasonic vibrators in the present invention.

The X-axis direction is an azimuthal direction. A Z-axis direction orthogonal to the X-axis direction is an elevational direction.

The backing layer 4 is provided on a surface of the ultrasonic vibrators 3 on a side opposite to the subject (on a side opposite to the acoustic lens 7). The backing layer 4 is thermally connected with the ultrasonic vibrators 3. The backing layer 4 is an exemplary embodiment of the backing layer in the present invention.

The backing layer 4 may be formed from a publicly known material for absorbing ultrasound transmitted from the ultrasonic vibrators 3 to a side opposite to the subject. Moreover, the backing layer 4 may be formed from a material having a thermal conductivity of 100 W/(m·K) or higher. For example, the backing layer 4 may be constructed of a material having a thermally conductivity in a range from 100 W/(m·K) to 300 W/(m·K).

The backing layer 4 may be of an inorganic material, for example, of graphite or aluminum. Moreover, the backing layer 4 may have an inhomogeneous structure capable of scattering ultrasound from the ultrasonic vibrators 3. More specifically, the backing layer 4 has an inhomogeneous structure at a level of the wavelength of ultrasound transmitted to the ultrasonic vibrators 3, for example, of a size of several tens of micrometers to one millimeter. By such an inhomogeneous structure, sound absorptivity can be ensured.

The thermal-conducting member 5 is disposed on a surface 4A of the backing layer 4 opposite to the ultrasonic vibrators 3. The thermal-conducting member 5 is an exemplary embodiment of the thermal-conducting member in the present invention. The thermal-conducting member 5 is thermally connected with the ultrasonic vibrators 3, so that heat generated in the ultrasonic vibrators 3 in transmitting/receiving ultrasound is transferred to the thermal-conducting member 5 via the backing layer 4.

Specifically, the thermal-conducting member 5 has a width smaller than the length of the backing layer 4 in the azimuthal direction, and is disposed in contact with a portion P (see FIG. 3) of the surface 4A of the backing layer 4. The portion P is a portion of the surface 4A in the azimuthal direction. The area of the portion P is one third or less of the total area of the surface 4A.

The thermal-conducting member 5 is a heat pipe in the present embodiment. Specifically, as shown in FIG. 3 in a partially enlarged view, the thermal-conducting member 5 has a cavity 50 in the inside in which a refrigerant is sealed.

The thermal-conducting member 5 is formed generally in a U shape. More specifically, the thermal-conducting member 5 has a base 51, and sides 52, 53 rising from both ends of the base 51. The base 51 is secured to the aforesaid surface 4A of the backing layer 4. The base 51 is an exemplary embodiment of the base in the present invention. The surface 4A of the backing layer 4 to which the base 51 is secured is an exemplary embodiment of the securing portion in the present invention.

The base 51 extends in the elevational direction along the portion P in the backing layer 4 in the condition that it is secured to the backing layer 4. The sides 52, 53 extend from the base 51 in a direction opposite to the backing layer 4 in the condition that the thermal-conducting member 5 is secured to the backing layer 4. In other words, the sides 52, 53 extend from the side of the ultrasonic vibrators 3 toward an end of the housing 2 on the side opposite to the ultrasonic vibrators 3. The sides 52, 53 constitute an exemplary embodiment of the first portion in the present invention.

The sides 52, 53 have respective first surfaces 52A, 53A facing the heat dissipation member 6. The first surfaces 52A, 53A constitute an exemplary embodiment of the first surface in the present invention. The first surfaces 52A, 53A are in contact with the inner surfaces of the heat dissipation member 6. More particularly, the first surface 52 is in contact with a first heat dissipation member 61 of the heat dissipation member 6, which will be discussed later. The second surface 53 is in contact with a second heat dissipation member 62 of the heat dissipation member 6, which will be discussed later. Thus, the thermal-conducting member 5 is thermally connected with the heat dissipation member 6 in the first surfaces 52A, 53A.

The heat dissipation member 6 is thermally connected with the ultrasonic vibrators 3 via the thermal-conducting member 5 by being thermally connected with the thermal-conducting member 5. The heat dissipation member 6 is comprised of the first heat dissipation member 61 and second heat dissipation member 62. The first heat dissipation member 61 is thermally connected with the side 52 of the thermal-conducting member 5, while the aforesaid second heat dissipation member is thermally connected with the side 53 of the thermal-conducting member 5. The heat dissipation member 6 is an exemplary embodiment of the heat dissipation member in the present invention. The first heat dissipation member 61 is an exemplary embodiment of the first heat dissipation member in the present invention, and the second heat dissipation member 62 is an exemplary embodiment of the second heat dissipation member in the present invention.

The first heat dissipation member 61 and second heat dissipation member 62 are constructed separately from the housing 2, and are formed from a material having thermal conductivity. For example, the first heat dissipation member 61 and second heat dissipation member 62 are formed from metal such as aluminum or copper.

The first heat dissipation member 61 and second heat dissipation member 62 have opposing surfaces 61A, 62A, respectively, facing inner surfaces 21C, 22C of the first housing member 21 and second housing member 22. The opposing surfaces 61A, 62A constitute an exemplary embodiment of the opposing surface in the present invention. The opposing surfaces 61A, 62A are formed into a shape conforming to the inner surfaces 21C, 22C of the first housing member 21 and second housing member 22, and have areas generally equal to those of the inner surfaces 21C, 22C, respectively. The first heat dissipation member 61 covers generally the whole inner surface 21C of the first housing member 21, and the second heat dissipation member 62 covers generally the whole inner surface 22C of the second housing member 22, thus causing the heat dissipation member 6 to have a shielding function.

Since the first heat dissipation member 61 and second heat dissipation member 62 have the opposing surfaces 61A, 62A formed into a shape conforming to the inner surfaces 21C, 22C of the first housing member 21 and second housing member 22, they are each formed generally into a C shape in a cross section orthogonal to the longitudinal direction of the housing 2. As shown in FIG. 4, the first heat dissipation member 61 and second heat dissipation member 62 are encased in the housing to overlap each other at respective open ends of the C-shaped cross section.

The first heat dissipation member 61 and second heat dissipation member 62 are secured in close contact with the inner surfaces 21C, 22C of the first housing member 21 and second housing member 22 at the opposing surfaces 61A, 62A. Thus, the heat dissipation member 62 is encased in the housing 2 while being thermally connected with the housing 2.

For example, the first heat dissipation member 61 and second heat dissipation member 62 are secured in close contact with the inner surfaces 21C, 22C of the first housing member 21 and second housing member 22 at the opposing surfaces 61A, 62A by thermal welding.

When the heat dissipation member 6 is secured to the housing 2 by thermal welding, the first housing member 21 and second housing member 22 are heated to a state in which they are thermally weldable to the first heat dissipation member 61 and second heat dissipation member 62. Then, the inner surface 21C of the heated first housing member 21 is thermally welded to the opposing surface 61A of the first heat dissipation member 61, and the inner surface 22C of the heated second housing member 22 is thermally welded to the opposing surface 62A of the second heat dissipation member 62.

When the heat dissipation member 6 is secured to the housing 2 by thermal welding, the opposing surfaces 61A, 62A of the first heat dissipation member 61 and second heat dissipation member 62 may be given asperities by an etching process.

In fabricating the housing 2, the first housing member 21 and second housing member 22 may be joined together at the joint interfaces 21B, 22B after the first heat dissipation member 61 and second heat dissipation member 62 are secured to them.

Heat generated in the ultrasonic vibrators 3 in transmitting/receiving ultrasound in the ultrasonic probe 1 in the present embodiment is transferred to the heat dissipation member 6 via the backing layer 4 and thermal-conducting member 5. The heat transferred to the heat dissipation member 6 is then dissipated over the whole heat dissipation member 6 via a portion in contact with the thermal-conducting member 5, and further transferred from the heat dissipation member 6 to the housing 2, and finally to the outside.

According to the ultrasonic probe 1 in the present embodiment described above, the housing 2 and heat dissipation member 6 are not monolithically molded by insert molding, and therefore, it is unnecessary to provide the heat dissipation member 6 with a hole or a notch otherwise required for insert molding. Thus, the heat dissipation area in the heat dissipation member 6 can be saved. Moreover, since the inner surfaces 21C, 22C of the housing 2 are secured in close contact to the opposing surfaces 61A, 62A of the heat dissipation member 6, mechanical strength can be improved, and moreover, heat can be efficiently transferred from the heat dissipation member 6 to the housing 2. Furthermore, since the inner surfaces 21C, 22C and opposing surfaces 61A, 62A are secured in close contact with one another by thermal welding without any intervening substance therebetween, heat transfer efficiency can be further improved.

While the present invention has been described with reference to the embodiments above, it will be easily recognized that the present invention may be practiced with several modifications without departing from scope and spirit thereof. For example, the first heat dissipation member 61 and second heat dissipation member 62 may be secured in close contact with the inner surfaces 21C, 22C of the first housing member 21 and second housing member 22 at the opposing surfaces 61A, 62A by adhesive boding. In this case, an adhesive material is applied to at least one of the inner surface 21C of the first housing member 21 and the opposing surface 61A of the first heat dissipation member 61, and in this condition, the inner surface 21C and opposing surface 61A are adhesively joined together. In addition, an adhesive material is applied to at least one of the inner surface 22C of the second housing member 22 and the opposing surface 62A of the second heat dissipation member 62, and in this condition, the inner surface 22C and the opposing surface 62A are adhesively joined together.

The ultrasonic probe may also be provided with a reflective layer disposed between, and moreover thermally connected to, the ultrasonic vibrators and backing layer, for reflecting ultrasound transmitted from the ultrasonic vibrators, although not specifically shown.

Moreover, while the opposing surfaces 61A, 62A of the first heat dissipation member 61 and second heat dissipation member 62 have areas generally equal to those of the inner surfaces 21C, 22C of the first housing member 21 and second housing member 22, they may have smaller areas than those. For example, the opposing surfaces 61A, 62A of the first heat dissipation member 61 and second heat dissipation member 62 only have to have areas of at least one third or more of the total area of the surface of the whole ultrasonic vibrators 3 on one side.

Furthermore, the opposing surface 61A of the first heat dissipation member 61 may have an area of at least one third or more of the area of the first surface 52A of the thermal-conducting member 5 in the side 52, and the opposing surface 62A of the second heat dissipation member 62 may have an area of at least one third or more of the area of the first surface 53A of the thermal-conducting member 5 in the side 53.

I claim:

1. An ultrasonic probe comprising:
   a plurality of ultrasonic vibrators for transmitting ultrasound;
   a backing layer disposed on the plurality of ultrasonic vibrators;
   a housing for encasing said plurality of ultrasonic vibrators;
   a heat dissipation member constructed separately from said housing, and encased in said housing in thermal connection with said plurality of ultrasonic vibrators and said housing, wherein
   said heat dissipation member has an opposing surface facing an inner surface of said housing, said opposing surface being secured in close contact with said inner surface, wherein said opposing surface is formed into a shape conforming to said inner surface of said housing, and wherein said opposing surface has an area generally equal to that of said inner surface of said housing; and
   a thermal-conducting member encased in said housing, said thermal-conducting member being thermally connected with said plurality of ultrasonic vibrators and said heat dissipation member, wherein the thermal-conducting member comprises a base secured to the backing layer and a plurality of sides extending from the base in a direction opposite to the backing layer, wherein said heat dissipation member is thermally connected with said ultrasonic vibrators via said thermal-conducting member.

2. The ultrasonic probe as recited in claim 1, wherein: said heat dissipation member is secured at said opposing surface in close contact with said inner surface of said housing through thermal welding.

3. The ultrasonic probe as recited in claim 1, wherein: said heat dissipation member is secured at said opposing surface in close contact with said inner surface of said housing by being adhesively bonded thereto.

4. The ultrasonic probe as recited in claim 1, wherein: said opposing surface has an area of at least one third or more of a surface area of said plurality of ultrasonic vibrators.

5. The ultrasonic probe as recited in claim 1, wherein: said heat dissipation member is formed from a material having thermal conductivity.

6. The ultrasonic probe as recited in claim 1, wherein: said heat dissipation member is formed from metal.

7. The ultrasonic probe of claim 1, wherein the backing layer has a length in an azimuthal direction, and wherein the thermal-conducting member has a width in the azimuthal direction that is smaller than the length of the backing layer in the azimuthal direction.

8. The ultrasonic probe of claim 1, wherein the thermal-conducting member is formed generally in a U-shape.

9. The ultrasonic probe of claim 7, wherein a first of the plurality of sides rises from a first end of the base and a second of the plurality of sides rises from a second end of the base.

10. The ultrasonic probe as recited in claim 1, wherein: said thermal-conducting member is a heat pipe.

11. The ultrasonic probe of claim 10, wherein the backing layer has a length in an azimuthal direction, and wherein the thermal-conducting member has a width in the azimuthal direction that is smaller than the length of the backing layer in the azimuthal direction.

12. The ultrasonic probe of claim 10, wherein the thermal-conducting member is formed generally in a U-shape.

13. The ultrasonic probe of claim 12, wherein a first of the plurality of sides rises from a first end of the base and a second of the plurality of sides rises from a second end of the base.

14. The ultrasonic probe as recited in claim 1, wherein: said backing layer is constructed of a material having thermal conductivity of 100 W/(m·K) or higher.

15. The ultrasonic probe as recited in claim 1, wherein: said heat dissipation member is comprised of a first heat dissipation member and a second heat dissipation member, and
    said first heat dissipation member and said second heat dissipation member are thermally connected with said first portion of said thermal-conducting member.

16. The ultrasonic probe as recited in claim 15, wherein: said housing is comprised of a first housing member and a second housing member,
    said first housing member and said second housing member are joined together at respective joint interfaces facing each other, and moreover
    said first housing member is thermally connected with said first heat dissipation member and said second housing member is thermally connected with said second heat dissipation member.

17. The ultrasonic probe as recited in claim 1, wherein: said heat dissipation member has a shielding function.

18. An ultrasonic image display apparatus comprising:
    a main unit comprising a transmission/reception beamformer, an echo data processing section, a display processing section, and a display device; and
    an ultrasonic probe comprising:
      a plurality of ultrasonic vibrators for transmitting ultrasound;
      a backing layer disposed on the plurality of ultrasonic vibrators;
      a housing for encasing said plurality of ultrasonic vibrators;
      a heat dissipation member constructed separately from said housing, and encased in said housing in thermal connection with said plurality of ultrasonic vibrators and said housing, wherein
      said heat dissipation member has an opposing surface facing an inner surface of said housing, said opposing surface being secured in close contact with said inner surface, wherein said opposing surface is formed into a shape conforming to said inner surface of said housing, and wherein said opposing surface has an area generally equal to that of said inner surface of said housing; and
      a thermal-conducting member encased in said housing, said thermal-conducting member being thermally connected with said plurality of ultrasonic vibrators and said heat dissipation member, wherein the thermal-conducting member comprises a base secured to the backing layer and a plurality of sides extending from the base in a direction opposite to the backing layer, wherein said heat dissipation member is thermally connected with said plurality of ultrasonic vibrators via said thermal-conducting member.

\* \* \* \* \*